United States Patent [19]

Matsushiro

[11] Patent Number: 5,468,479
[45] Date of Patent: Nov. 21, 1995

[54] COMPOSITIONS CONTAINING LACTIC ACID BACTERIUM *STREPTOCOCCUS SALIVARIUS*

[75] Inventor: Aizo Matsushiro, Osaka, Japan

[73] Assignees: Toshio Kawanishi, Kobe; Kazusumi Tsutsumi, Osaka, both of Japan

[21] Appl. No.: 905,279

[22] Filed: Jun. 26, 1992

[30] Foreign Application Priority Data

Jun. 28, 1991 [JP] Japan .................................. 3-158033

[51] Int. Cl.$^6$ .......................... A01N 63/00; A61K 47/00; A23L 1/28; C12N 9/46
[52] U.S. Cl. ...................... 424/93.44; 424/50; 424/439; 426/61; 426/531; 435/211; 435/253.4; 435/885
[58] Field of Search ................... 424/439, 50, 93 H, 424/93.44; 195/65; 435/211, 253.4, 853, 885; 426/2, 61, 531

[56] References Cited

U.S. PATENT DOCUMENTS

| | | | |
|---|---|---|---|
| 3,912,594 | 10/1975 | Shimada et al. | 195/65 |
| 3,929,579 | 12/1975 | Yoshimura et al. | 195/62 |
| 4,255,414 | 3/1981 | Lembke et al. | 424/50 |
| 4,710,379 | 12/1987 | Kawai et al. | 424/93 H |
| 5,135,739 | 8/1992 | Tsurumizu et al. | 424/50 |
| 5,225,344 | 7/1993 | Tsurumizu et al. | 435/353.4 |
| 5,306,639 | 4/1994 | Matsushiro | 435/320.1 |

FOREIGN PATENT DOCUMENTS

| | | | |
|---|---|---|---|
| 0154549 | 9/1985 | European Pat. Off. | 435/253.4 |
| 0195672A3 | 9/1986 | European Pat. Off. . | |
| 0440409 | 8/1991 | European Pat. Off. | 424/93 H |
| 58-164517 | 9/1983 | Japan . | |

OTHER PUBLICATIONS

"Synthesis and degradation of intracellular polyglucose in *Streptococcus salivarius*", Hamilton, 1968, pp. 65–76, J. of Microbio. v. 15.
"Studies w/fluride, etc. . . . ", Hamilton, 1969, pp. 1013–1019, J. of Microbiology.
Japanese Document No. JP–58–164517 abstract, 1983.
Donkersloot, et al., *Journal of Clinical Microbiology*, "More Sensitive Test Agar for Detection of Dextranase–Producing Oral Streptococci and Identification of Two Glucan Synthesis–Defective Dextranase Mutants of *Streptococcus mutans* 6715," Dec. 1979, vol. 10, No. 6, pp. 919–922.
Lawman, et al., *Journal of Bacteriology*, "Molecular Cloning of the Extracellular Endodextranase of *Streptococcus salivarious*," Dec. 1991, vol. 173, No. 23, pp. 7423–7428.
Lawman, et al., *Journal of General Microbiology*, "Multi-level control of extracellular sucrose metabolism in *Streptococcus salivarius* by sucrose," 1991, vol. 137, pp. 5–13.

*Primary Examiner*—John W. Rollins
*Assistant Examiner*—Deborah K. Ware
*Attorney, Agent, or Firm*—Marshall, O'Toole, Gerstein, Murray & Borun

[57] ABSTRACT

Disclosed are compositions such as foods and pharmaceuticals, and methods of their production, comprising at least one lactic acid bacterium capable of assisting in intestinal regulation and preventing dental caries. The bacterium is an isolated living *Streptococcus salivarius* strain identified as FERM BP-3885 and is further capable of producing dextranase while persisting in the oral cavity.

3 Claims, 2 Drawing Sheets

| STRAIN | DEXTRANASE ACTIVITY | SHAPE OF THE COLONY | |
|---|---|---|---|
| | | 30 HOURS CULTURE | 48 HOURS CULTURE |
| M-06 | + |  |  |
| M-17 | − |  |  |
| M-33 (FERM BP-3885) | +++ |  |  |
| G8326 | +++ |  |  |
| 13956 | + |  |  |
| HHT | ± |  |  |
| HT9R | ± |  |  |
| HT19 | ∓ |  |  |
| HT32 | + |  |  |
| HT59 | ∓ |  |  |
FIG.2

COMPOSITIONS CONTAINING LACTIC ACID BACTERIUM *STREPTOCOCCUS SALIVARIUS*

BACKGROUND OF THE INVENTION

The present invention relates generally to compositions containing lactic acid bacteria and more specifically to compositions which are capable of assisting in intestinal regulation and which have the additional property of prevention of dental caries. The invention also relates to the methods of producing such compounds.

The term, "lactic acid bacteria", is a trivial name given to a diverse group of bacteria which are characterized by the production of lactic acid during the fermentation of carbohydrates. It is widely known that food products, such as yogurt, and pharmaceuticals, such as BIOFERMIN™, contain lactic acid bacteria. Among the lactic acid bacteria contained in such food product and pharmaceutical compositions are *Streptococcus lactis, Streptococcus faecalis, Lactobacillus casei, Lactobacillus acidophilus* and *Lactobacillus bifidus*. These bacteria are also characterized by their ability to aid in intestinal regulation, in part because such bacteria tend to remain in the human intestinal flora for relatively long periods after consumption.

The bacterial flora indigenous to the oral cavity vary continuously and consist of a variety of bacterial species. Among the bacteria indigenous to the oral cavity, the following species are classified as lactic acid bacteria by Bergey's Manual of Systematic Bacteriology: Vol. 2 (Williams & Wilkins, eds. 1986): *Streptococcus salivarius, Streptococcus sangius, Streptococcus mitior, Streptococcus milleri, Streptococcus mutans, Streptococcus rattus, Streptococcus cricetus, Streptococcus sobrinus, Streptococcus ferus, Streptococcus oralis*, and *Streptococcus mills*.

Of interest to the present invention is my U.S. Ser. No. 07/772,850 filed on Oct. 8, 1991, now U.S. Pat. No. 5,306, 639, wherein genetically transformed *Streptococcus sanguis* produced dextranase and glucanase which are useful in degrading insoluble glucan, the causative agent in the formation of dental plaque in the oral cavity.

Since the oral cavity is part of the human digestive track, it was hypothesized that enteric bacteria, such as those described above, may have effects (e.g., dental caries prevention) other than intestinal regulation and that such effects may be determined by culturing those bacteria which are also indigenous to the oral cavity.

BRIEF SUMMARY OF THE INVENTION

The present invention provides novel compositions, such as foods and pharmaceuticals, which contain at least one lactic acid bacterium which produces extracellular dextranase. Thus, compositions according to the present invention possess the novel property of preventing dental caries while, at the same time, aiding the regulation of the intestinal flora.

The present invention also contemplates methods of producing such compositions in the form of an ingestible composition, such as a food product or a pharmaceutical product or the like, comprising the aforementioned lactic acid bacteria which are capable of persisting in the human oral cavity and which produce enzymes capable of degrading dental plaque. Also contemplated are food product or pharmaceutical product compositions which contain, in addition to the lactic acid bacteria of the invention, other lactic acid bacteria conventionally employed in such compositions.

Compositions according to the present invention preferably contain a lactic acid bacterium which is not a human pathogen and more preferably contain the non-pathogenic lactic acid bacterium, *Streptococcus salivarius*. Most preferably, a strain of *Streptococcus salivarius* which produces dextranase and which does not produce insoluble glucan is used in the compositions of the invention. One such strain, *Streptococcus salivarius* M-33 was received for deposit by the Fermentation Research Institute, Ibaraki-ken, Japan on Jun. 26, 1991 with the accession number FERM BP-3885.

BRIEF DESCRIPTION OF THE DRAWING

FIG. 2 represents the results of tests to screen various bacterial strains for utility in compositions of the invention.

DETAILED DESCRIPTION OF THE INVENTION

Figure 1:
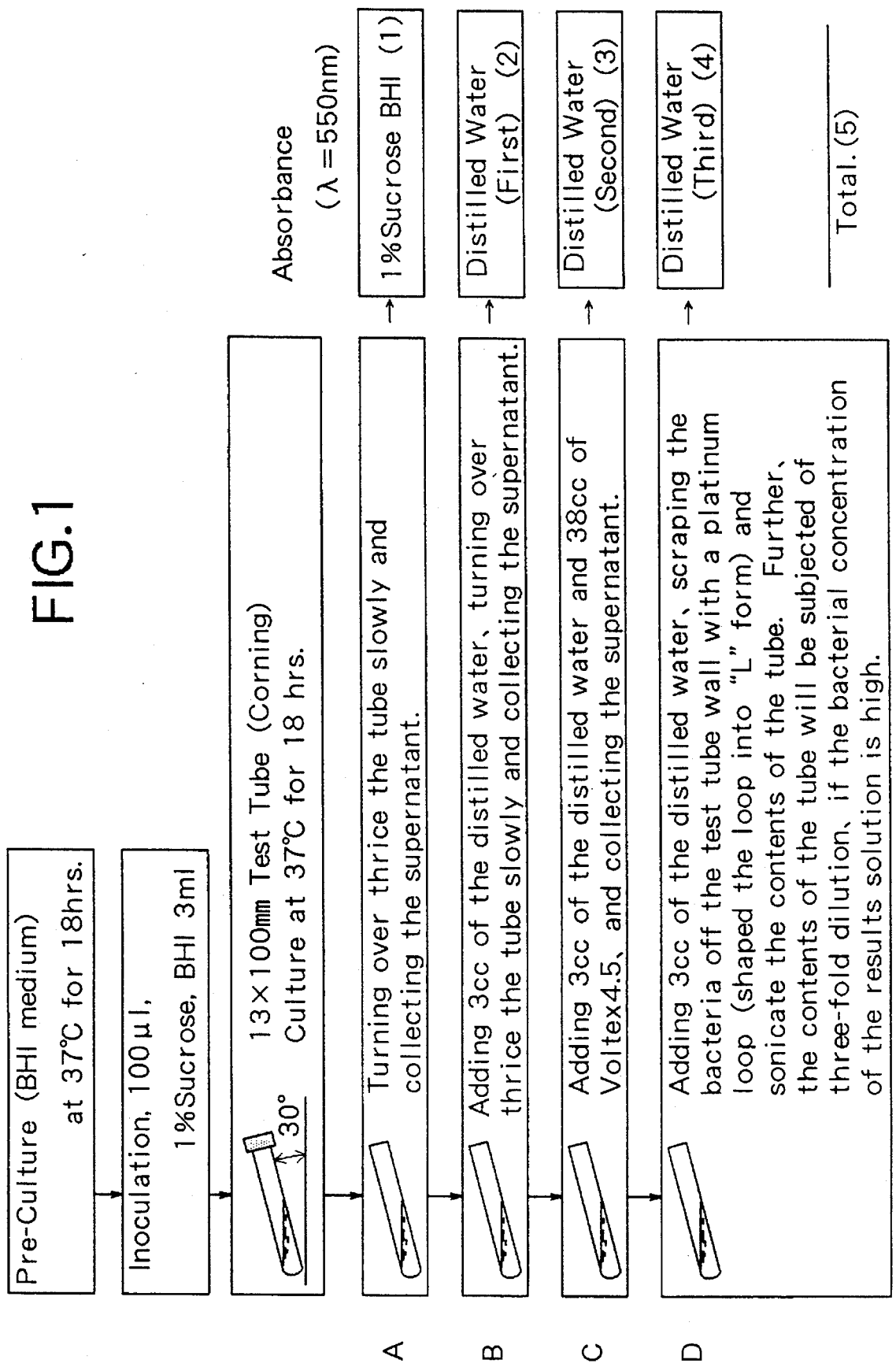
FIG. 1 represents a schematic diagram of an experimental method to determine the effectiveness of lactic acid bacteria useful in the invention in degrading dental plaque.

Example 1 describes the screening of various strains of *Streptococcus salivarius* for dextranase activity. Example 2 demonstrates the ability of various strains of *Streptococcus salivarius* to degrade dental plaque. Example 3 relates to the relationship between the extent of dextranase activity of *Streptococcus salivarius* and the resulting shape of the bacterial colony.

EXAMPLE 1

Of the various above-noted bacterial species listed as lactic acid bacteria in Bergy's Manual, only *Streptococcus salivarius* is non-pathogenic and indigenous to the human oral cavity. This species also varies from strain to strain in its capacity to produce insoluble glucan (dextran). The dextranase activity of ten strains of *Streptococcus salivarius* obtained from the principal strain preservation institution of Japan was determined by inoculating samples of each strain onto a MITIS-SALIVARIUS AGAR (Difco) to which 1% Chapman Solution was added. The shape of the bacterial colony was determined 30 hours and 48 hours after inoculation. The same ten strains were then inoculated onto Todd Hewitt Broth (Difco) to which 0.2% Blue Dextran was added. The relative extent of dextranase activity was determined on the basis of the size of the transparent halo formed around the bacterial colony 48 hours after inoculation. The relative size of the halo was assigned a score ranging from none(–) to very large(+++). The results, shown in FIG. 2, again indicate that strain M-33 and strain G8326 produced the highest amount of dextranase activity and produced crater-shaped colonies after 48 hours. Strain M-33 of *Streptococcus salivarius* was seen to possess potent dextranase activity on par with the recombinant-produced *Streptococcus sanguis* (pMNK-4). In view of the high level of dextranase activity possessed by *Streptococcus salivarius*, that strain was further tested for use as the lactic acid bacteria component of the compositions according to the invention for degradation of dental plaque.

EXAMPLE 2

An experiment was conducted to test the ability of *Streptococcus salivarius* M-33 to eliminate dental plaque according to the protocol set forth in FIG. 1. *Streptococcus sobrinus* 6715, a cariogenic bacterium, was precultured on brain heart infusion medium (Difco) at 37° C. for 18 hours.

A 50 μl sample of the preculture medium was then inoculated onto 3 ml of brain heart infusion medium supplemented with 1% sucrose for the control culture. Test co-cultures further included either 50 ul of *Streptococcus salivarius* M-33 or G8326 preculture medium. A static culture was maintained at 37° C. in a 13×100 mm test tube (Corning) sloped at an angle of 30 degrees. After 18 hours, the amount of insoluble glucan (dental plaque) adhered to the test tube wall was measured spectrophotometrically as a function of absorbance of insoluble glucan at 550 nm. Testing was done a total of four consecutive times. The first test was conducted by turning the test tube slowly three times, collecting the supernatant, and determining its absorbance. Three ml of distilled water was then added to the test tube which was then turned slowly three times. The supernatant was again collected for the second absorbance measurement. Three ml of distilled water and 38 ml of Voltex 4.5 was added, the tube was vortexed, and the supernatant was collected as the third sample for absorbance screening. Finally, three mls of distilled water was added to the test tube and bacteria were scraped off the test tube wall with a platinum loop. The test tube was then sonicated, subjected to a three fold dilution (if the bacterial concentration of the solution was too high), and the fourth absorbance measurement was taken. The sum of all previous absorbance readings was determined. The results of this experiment are presented in Table 1.

TABLE 1

| Culture System | (1) | (2) | (3) | (4) | Total (5) | (3)/(5) (loose) | (4)/(5) (firm) | [(3) + (4)] (5) |
|---|---|---|---|---|---|---|---|---|
| mono-culture of 6715 | 0 | 0.0108 | 0.257 | 0.734 | 1.002 | 24.90 | 74.04 | 98.94 |
| co-culture of 6715 and M-33 | 0.26 | 0.27 | 0.91 | 0.50 | 1.93 | 47.36 | 25.72 | 73.08 |
| co-culture of 6715 and G8326 | 0.36 | 0.18 | 0.54 | 0.72 | 1.80 | 30.02 | 40.61 | 70.63 |

Any insoluble glucan absorbance obtained in the first two rinses (i.e., columns 1 and 2 of Table 1) is considered to be obtained by the rinse and does not fall in the category of dental plaque. The insoluble glucan obtained in the third wash, column 3 of Table 1, is "fragile" dental plaque and referred to as "loose." The insoluble glucan of column 4 is terms "firm" dental plaque, which can only be obtained by sonication as provided above. The results of Table 1 indicate that dental plaque formed in the mono-culture of *Streptococcus sobrinas* 6715, the cariogenic bacterium, consists mostly of "firm" insoluble glucan.

As shown in Table 1, the results of coculture with *Streptococcus salivarius* M-33 indicate that much less "firm" dental plaque was present. Instead, there was a greater proportion of "rinse" and "loose" plaque. Similar results were obtained when *Streptococcus salivarius* G8326 was incubated with *Streptococcus sobrinas* 6715. From the foregoing data, it can be inferred that *Streptococcus salivarius* M-33 and *Streptococcus salivarius* G8326 possess significant dextranase activity, resulting in a reduction in the dental plaque formed by *Streptococcus sobrinas* 6715.

EXAMPLE 3

The results of Examples 1 and 2 indicate that strains of lactic acid bacteria, specifically those of *Streptococcus salivarius*, have increased dextranase activity. Additional experiments were then conducted to further characterize the strains of *Streptococcus salivarius* capable of reducing dental plaque.

Both *Streptococcus salivarius* M-33 and *Streptococcus salivarius* G8326 were inoculated, as in Example 1 onto a MITIS-SALVARIUS Agar Plate to which 1% Chapman Solution had been added. Each plate was incubated at 37° C. for about 30 hours, at which time most of the evident colonies possessed the large smooth structure typical of these bacteria as indicated in the left hand column (30 hours) of FIG. 2. After about 48 hours of incubation, the center of the colonies of *Streptococcus salivarius* M-33 or *Streptococcus salivarius* G8326 formed a crater like configuration, indicating that the insoluble glucan on the plate had been degraded.

When the same procedure was conducted using other strains, such as *Streptococcus salivarius*, which has weak dextranase activity, the formation of crater like configurations was not observed. Thus, the results of the experiments indicated that there is a high degree of correlation between the amount of dextranase activity and the observable appearance of bacterial colonies on MITIS-SALIVARIUS Agar plates. This correlation may be understood on the basis that *Streptococcus salivarius* produced, as an extracellular polysaccharide, a water soluble fructan (levan) and a water insoluble glucan (dextran). Since these polysaccharides were produced as the cells multiplied, their accumulation caused the formation of the raised, glossy smooth colonies seen in the absence of dextranase. In the presence of *Streptococcus salivarius* M-33 or *Streptococcus salivarius* G8326 colonies, the extracellular dextran was broken down by the dextranase produced in those colonies, causing the crater like configuration of the colony after 48 hours or more of incubation.

Food and pharmaceutical compositions according to the invention are prepared in the same manner as other lactic acid bacteria compositions known in the art, with dextranase-producing bacteria replacing or supplementing bacteria ordinarily incorporated therein.

Numerous modifications and variations in the invention as above-described are expected to occur to those of ordinary skill in the art upon consideration of the above-illustrated examples and consequently only such limitations as appear in the appended claims should be placed on the scope of the invention.

I claim:

1. An ingestible composition comprising a biologically pure live *Streptococcus salivarius* M-33 deposited as accession number FERM BP-3885 which persists in the oral cavity and which produces dextranase.

2. The composition according to claim 1 wherein the composition is contained in a food.

3. The composition according to claim 2 further comprising a pharmaceutically acceptable carrier.

* * * * *